United States Patent
Kawamura

(10) Patent No.: US 10,810,710 B2
(45) Date of Patent: Oct. 20, 2020

(54) RADIOGRAPHIC IMAGE PROCESSING APPARATUS, RADIOGRAPHIC IMAGE PROCESSING METHOD, AND RADIOGRAPHIC IMAGE PROCESSING PROGRAM

(71) Applicant: FUJIFILM CORPORATION, Minato-ku, Tokyo (JP)

(72) Inventor: Takahiro Kawamura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 137 days.

(21) Appl. No.: 15/920,460

(22) Filed: Mar. 14, 2018

(65) Prior Publication Data
US 2018/0293715 A1    Oct. 11, 2018

(30) Foreign Application Priority Data

Apr. 11, 2017 (JP) .................................. 2017-077995

(51) Int. Cl.
*G01T 1/16* (2006.01)
*G06T 5/00* (2006.01)
(Continued)

(52) U.S. Cl.
CPC ............ *G06T 5/003* (2013.01); *A61B 6/4266* (2013.01); *A61B 6/5241* (2013.01);
(Continued)

(58) Field of Classification Search
CPC .. A61B 6/00; A61B 6/02; A61B 6/022; A61B 6/03; A61B 6/40; A61B 6/4035; A61B 6/405; A61B 6/4064; A61B 6/4071
See application file for complete search history.

(56) References Cited

U.S. PATENT DOCUMENTS

2007/0216951 A1    9/2007  Shiraishi
2008/0061395 A1 *  3/2008  Tkaczyk ................ A61B 6/032
                                                                257/443
(Continued)

FOREIGN PATENT DOCUMENTS

JP    H09-197585 A    7/1997
JP    H09-294738 A    11/1997
(Continued)

OTHER PUBLICATIONS

English language translation of the following: Office action dated Aug. 4, 2020 from the JPO in a Japanese patent application No. 2017-077995 corresponding to the instant patent application. This office action translation is submitted now in order to supplement the understanding of the cited references which are being disclosed in the instant Information Disclosure Statement.

*Primary Examiner* — David P Porta
*Assistant Examiner* — Mamadou Faye
(74) *Attorney, Agent, or Firm* — Solaris Intellectual Property Group, PLLC

(57) ABSTRACT

An image acquisition unit acquires first and second radiographic images acquired by irradiating a first radiation detector and a second radiation detector which overlaps the first radiation detector so as to deviate from the first radiation detector by a half pixel with radiation which has been emitted from a radiation source and transmitted through an object. A corresponding positional relationship acquisition unit acquires a corresponding positional relationship between the position of pixels of the first radiographic image and the position of pixels of the second radiographic image. A resolution enhancement unit estimates a pixel value corresponding to a position between the pixels of the first radiographic image, on the basis of the corresponding positional relationship, a pixel value of the first radiographic image, and a pixel value of the second radiographic image, (Continued)

and generates a processed radiographic image having a higher resolution than the first and second radiographic images.

6 Claims, 4 Drawing Sheets

(51) Int. Cl.
    *A61B 6/00*           (2006.01)
    *G06T 5/50*           (2006.01)
    *G01N 23/04*          (2018.01)
    *G06T 3/40*           (2006.01)

(52) U.S. Cl.
    CPC .......... *A61B 6/5258* (2013.01); *G01N 23/04* (2013.01); *G06T 3/4069* (2013.01); *G06T 5/002* (2013.01); *G06T 5/50* (2013.01); *G01N 2223/401* (2013.01); *G01N 2223/42* (2013.01); *G06T 2207/10116* (2013.01); *G06T 2207/10124* (2013.01); *G06T 2207/20182* (2013.01); *G06T 2207/20216* (2013.01); *G06T 2207/30068* (2013.01)

(56) References Cited

U.S. PATENT DOCUMENTS

2014/0138553 A1*   5/2014   Ogawa .................... A61B 6/14
                                                       250/393
2015/0319363 A1    11/2015   Furukawa

FOREIGN PATENT DOCUMENTS

| | | |
|---|---|---|
| JP | 2001-145617 A | 5/2001 |
| JP | 2007-251860 A | 9/2007 |
| JP | 2015-097590 A | 5/2015 |
| JP | 2015-192199 A | 11/2015 |

* cited by examiner

RADIOGRAPHIC IMAGE PROCESSING APPARATUS, RADIOGRAPHIC IMAGE PROCESSING METHOD, AND RADIOGRAPHIC IMAGE PROCESSING PROGRAM

CROSS REFERENCE TO RELATED APPLICATIONS

The present application claims priority under 35 U.S.C. § 119 to Japanese Patent Application No. 2017-077995 filed on Apr. 11, 2017. The above application is hereby expressly incorporated by reference, in its entirety, into the present application.

BACKGROUND

Field of the Invention

The present invention relates to a radiographic image processing apparatus, a radiographic image processing method, and a radiographic image processing program that generate a high-quality radiographic image using two radiographic images.

Related Art

In the related art, a process of improving the sharpness and granularity of a radiographic image has been performed in order to improve the quality of the radiographic image. For this purpose, the following image processing is performed: a process of increasing the sensitivity of a detector for detecting a radiographic image transmitted through an object; a sharpness enhancement process for a radiographic image; and a smoothing process for improving granularity.

For example, JP2015-097590A discloses a method which acquires one high-resolution radiographic image using two mammographic images. In addition, JP1997-197585A (JP-H09-197585A) discloses a method which performs imaging with two detectors overlapping each other to acquire two radiographic images, aligns two radiographic images, and adds the two radiographic images to acquire one radiographic image with high sharpness. Furthermore, JP1997-294738A (JP-H09-294738A) discloses a method which performs imaging with two detectors overlapping each other to acquire two radiographic images, adjusts the number of pixels of one of the radiographic images so as to be one fourth of the number of pixels of the other radiographic image, generates a radiographic image having the same number of pixels as the other radiographic image, and adds two radiographic images to acquire a radiographic image with improved granularity and an improved S/N ratio.

In a case in which the amount of radiation emitted to the radiation detector increases, the sharpness and granularity of the acquired radiographic image are improved. However, in a case in which the amount of radiation emitted to the radiation detector increases, the amount of radiation emitted to the object increases. In addition, a technique is considered which increases the pixel size of a radiation detector such that the amount of radiation emitted to a unit area of the detector increases, in order to improve granularity, without increasing the amount of radiation emitted to the object. However, in a case in which the pixel size increases, spatial resolution is reduced and thus the sharpness of the acquired radiographic image is reduced.

The invention has been made in view of the above-mentioned problems and an object of the invention is to acquire a radiographic image with improved sharpness and granularity, without increasing the amount of radiation emitted to an object.

SUMMARY

A radiographic image processing apparatus according to the invention comprises: image acquisition unit for acquiring a first radiographic image and a second radiographic image acquired from first detection unit and second detection unit which overlaps the first detection unit so as to deviate from the first detection unit by a half pixel, respectively, by irradiating the first detection unit and the second detection unit with radiation which has been emitted from a radiation source and transmitted through an object; corresponding positional relationship acquisition unit for acquiring a corresponding positional relationship between a position of pixels of the first radiographic image and a position of pixels of the second radiographic image; and resolution enhancement unit for estimating a pixel value corresponding to a position between the pixels of the first radiographic image, on the basis of the corresponding positional relationship, a pixel value of the first radiographic image, and a pixel value of the second radiographic image, and generating a processed radiographic image having a higher resolution than the first and second radiographic images.

The term "overlap with a deviation of a half pixel" means that the second detection unit overlaps the first detection unit so as to deviate from the first detection unit by a distance corresponding to half of the pixel size of the first and second detection unit. In addition, since the pixels are two-dimensionally arranged in the first and second detection unit, the term "deviation by a half pixel" means that one detection unit deviates from the other detection unit by a distance corresponding to a half pixel in the vertical and horizontal directions in which the pixels of the first and second detection unit are arranged.

In the radiographic image processing apparatus according to the invention, the resolution enhancement unit may weight the pixel values of the first radiographic image and the second radiographic image according to a distance between the position between the pixels of the first radiographic image and at least one pixel, which corresponds to the position between the pixels of the first radiographic image, in the second radiographic image and may estimate the pixel value corresponding to the position between the pixels of the first radiographic image.

In the radiographic image processing apparatus according to the invention, a pixel size of the first and second detection unit may be equal to or greater than 200 μm and equal to or less than 400 μm.

The radiographic image processing apparatus according to the invention may further comprise reduction unit for performing filtering for the processed radiographic image, using a smoothing filter, and reducing a size of the processed radiographic image so as to be equal to a size of the first radiographic image or the second radiographic image to generate a reduced radiographic image.

A radiographic image processing method according to the invention comprises: acquiring a first radiographic image and a second radiographic image acquired from first detection unit and second detection unit which overlaps the first detection unit so as to deviate from the first detection unit by a half pixel, respectively, by irradiating the first detection unit and the second detection unit with radiation which has been emitted from a radiation source and transmitted through an object; acquiring a corresponding positional relationship between a position of pixels of the first radiographic image and a position of pixels of the second radiographic image; and estimating a pixel value corresponding to a position between the pixels of the first radiographic image, on the basis of the corresponding positional relationship, a pixel value of the first radiographic image, and a pixel value of the second radiographic image, and generating a processed radiographic image having a higher resolution than the first and second radiographic images.

In addition, the invention may provide a program that causes a computer to perform the radiographic image processing method according to the invention.

Another radiographic image processing apparatus according to the invention includes a memory that stores commands to be executed by a computer and a processor that is configured to execute the stored commands. The processor acquires a first radiographic image and a second radiographic image acquired from first detection unit and second detection unit which overlaps the first detection unit so as to deviate from the first detection unit by a half pixel, respectively, by irradiating the first detection unit and the second detection unit with radiation which has been emitted from a radiation source and transmitted through an object. The processor acquires a corresponding positional relationship between a position of pixels of the first radiographic image and a position of pixels of the second radiographic image. The processor estimates a pixel value corresponding to a position between the pixels of the first radiographic image, on the basis of the corresponding positional relationship, a pixel value of the first radiographic image, and a pixel value of the second radiographic image, and generates a processed radiographic image having a higher resolution than the first and second radiographic images.

According to the invention, the first radiographic image and the second radiographic image acquired from the first detection unit and the second detection unit which overlaps the first detection unit so as to deviate from the first detection unit by a half pixel, respectively, by irradiating the first detection unit and the second detection unit with radiation which has been emitted from the radiation source and transmitted through the object are acquired. The corresponding positional relationship between the position of the pixels of the first radiographic image and the position of the pixels of the second radiographic image is acquired. A pixel value corresponding to the position between the pixels of the first radiographic image is estimated on the basis of the corresponding positional relationship, the pixel value of the first radiographic image, and the pixel value of the second radiographic image. A processed radiographic image having a higher resolution than the first and second radiographic images is generated. Here, since the first and second detection unit overlap each other so as to deviate by a half pixel, the probability that each pixel of the second radiographic image will be located between the pixels of the first radiographic image is high. Therefore, the use of the pixel value of the second radiographic image makes it possible to generate a processed image with high resolution and high sharpness, without increasing the amount of radiation emitted to an object.

DETAILED DESCRIPTION

Figure 1:
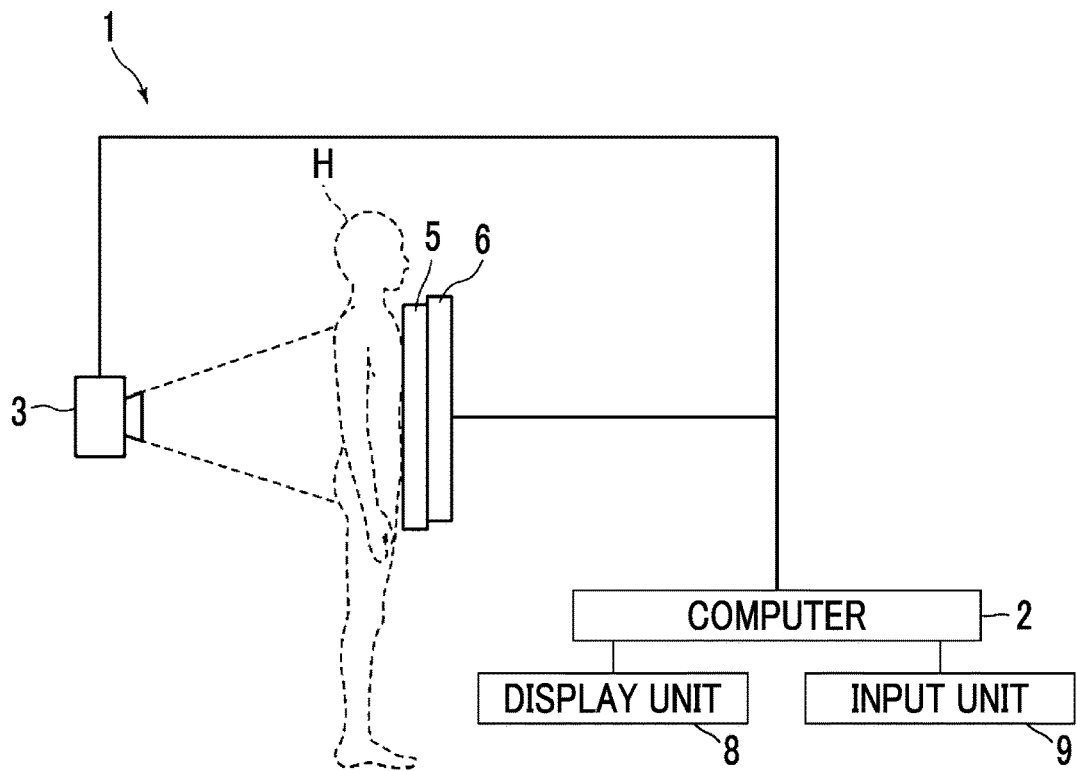
FIG. 1 is a block diagram schematically illustrating the configuration of a radiography system to which a radiographic image processing apparatus according to a first embodiment of the invention is applied.

Hereinafter, embodiments of the invention will be described with reference to the drawings. FIG. 1 is a block diagram schematically illustrating the configuration of a radiography system to which a radiographic image processing apparatus according to a first embodiment of the invention is applied. As illustrated in FIG. 1, the radiography system according to the first embodiment captures two radiographic images, generates one processed high-quality radiographic image using the two radiographic images, and includes an imaging apparatus 1 and a computer 2 including the radiographic image processing apparatus according to this embodiment.

The imaging apparatus 1 irradiates a first radiation detector 5 and a second radiation detector 6 with X-rays that have been emitted from an X-ray source 3, which is a radiation source, and then transmitted through an object H and acquires two radiographic images using one imaging operation. During an imaging operation, as illustrated in FIG. 1, the first radiation detector 5 and the second radiation detector 6 are disposed in this order from the X-ray source 3 and the X-ray source 3 is driven. In addition, the first radiation detector 5 and the second radiation detector 6 overlap each other so as to deviate by a half pixel, as will be described below. The first and second radiation detectors 5 and 6 correspond to first and second detection unit.

With this configuration, the first radiation detector 5 acquires a first radiographic image G1 of the object H formed by the X-rays transmitted through the object H. In addition, the second radiation detector 6 acquires a second radiographic image G2 of the object H formed by the X-rays transmitted through the object H. The first and second radiographic images G1 and G2 are input to the computer 2 which is the radiographic image processing apparatus.

The first and second radiation detectors 5 and 6 can repeatedly record and read out radiographic images and may be so-called direct radiation detectors that directly receive emitted radiation and generate charge or so-called indirect radiation detectors that convert radiation into visible light and convert the visible light into a charge signal. Preferably, the following method is used as a radiographic image signal reading method: a so-called thin film transistor (TFT) reading method that turns on and off a TFT switch to read out a radiographic image signal; or a so-called optical reading method that emits reading light to read out a radiographic image signal. However, the radiographic image signal reading method is not limited thereto and other methods may be used.

A display unit 8 and an input unit 9 are connected to the computer 2. The display unit 8 is, for example, a cathode ray tube (CRT) or a liquid crystal display and assists the input of a captured radiographic image and various kinds of data required for processes performed in the computer 2. The input unit 9 includes, for example, a keyboard, a mouse, or a touch panel. The display unit 8 corresponds to display unit.

A radiographic image processing program according to this embodiment is installed in the computer 2. In this embodiment, the computer may be a workstation or a personal computer that is directly operated by an operator or a server computer that is connected to the workstation or the personal computer through a network. The radiographic image processing program is recorded on a recording medium, such as a digital versatile disk (DVD) or a compact disc read only memory (CD-ROM), is distributed, and is installed in the computer from the recording medium. Alternatively, the radiographic image processing program is stored in a storage device of a server computer connected to the network or a network storage in a state in which it can be accessed from the outside, is downloaded to the computer by request, and is installed.

Figure 2:
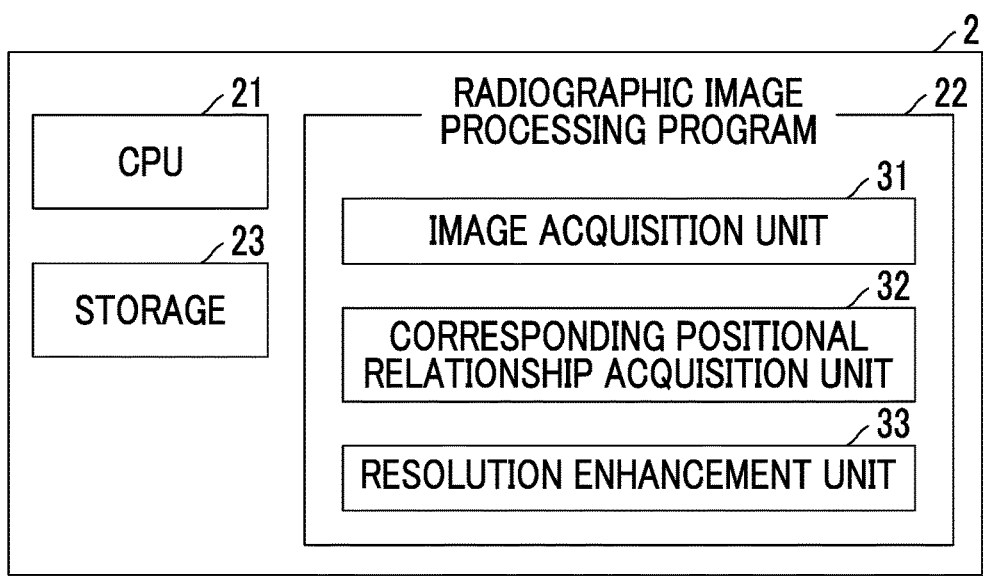
FIG. 2 is a diagram schematically illustrating the configuration of the radiographic image processing apparatus according to the first embodiment.

FIG. 2 is a diagram schematically illustrating the configuration of the radiographic image processing apparatus implemented by installing the radiographic image processing program in the computer 2 in the first embodiment. As illustrated in FIG. 2, the radiographic image processing apparatus includes a central processing unit (CPU) 21, a memory 22, and a storage 23 as a standard computer configuration.

The storage 23 is a storage device, such as a hard disk or a solid state drive (SSD), and stores a program for driving each unit of the imaging apparatus 1 and various kinds of information including the radiographic image processing program. In addition, the storage 23 stores captured radiographic images.

For example, the programs stored in the storage 23 are temporarily stored in the memory 22 in order to direct the CPU 21 to perform various processes. The radiographic image processing program defines, as the processes performed by the CPU 21, an image acquisition process that acquires the first radiographic image G1 and the second radiographic image G2 acquired from the first radiation detector 5 and the second radiation detector 6, respectively, by irradiating the first and second radiation detectors 5 and 6 with the X-rays which have been emitted from the X-ray source 3 and then transmitted through the object H, a corresponding positional relationship acquisition process that acquires a corresponding positional relationship between the position of pixels of the first radiographic image G1 and the position of pixels of the second radiographic image G2, and a resolution enhancement process that estimates a pixel value corresponding to the position between the pixels of the first radiographic image G1 on the basis of the corresponding positional relationship and the pixel values of the first and second radiographic images G1 and G2 and generates a processed radiographic image Gp having a higher resolution than the first and second radiographic images G1 and G2.

Then, the CPU 21 performs these processes according to the radiographic image processing program to cause the computer 2 to function as an image acquisition unit 31, a corresponding positional relationship acquisition unit 32, and a resolution enhancement unit 33. The computer 2 may include processors or processing circuits that perform the image acquisition process, the corresponding positional relationship acquisition process, and the resolution enhancement process. The processor or the processing circuit is not limited to a general-purpose processor or processing circuit and may be a dedicated circuit such as a field programmable gate array (FPGA) or an application specific integrated circuit (ASIC).

Here, in this embodiment, the pixel size of the first and second radiation detectors 5 and 6 is larger than the pixel size of the radiation detector according to the related art. In general, in a case in which a general radiographic image is acquired, the pixel size of the radiation detector is in the range of about 100 μm to about 200 μm. In addition, in mammography, since an image with a higher resolution is required, the pixel size is about 50 μm. The pixel size indicates the length of one side of a pixel. In a case in which the pixel size of the general radiation detector is a reference pixel size, in this embodiment, the pixel size is equal to or greater than two times the reference pixel size and is specifically equal to or greater than 200 μm and equal to or less than 400 μm.

Figure 3:
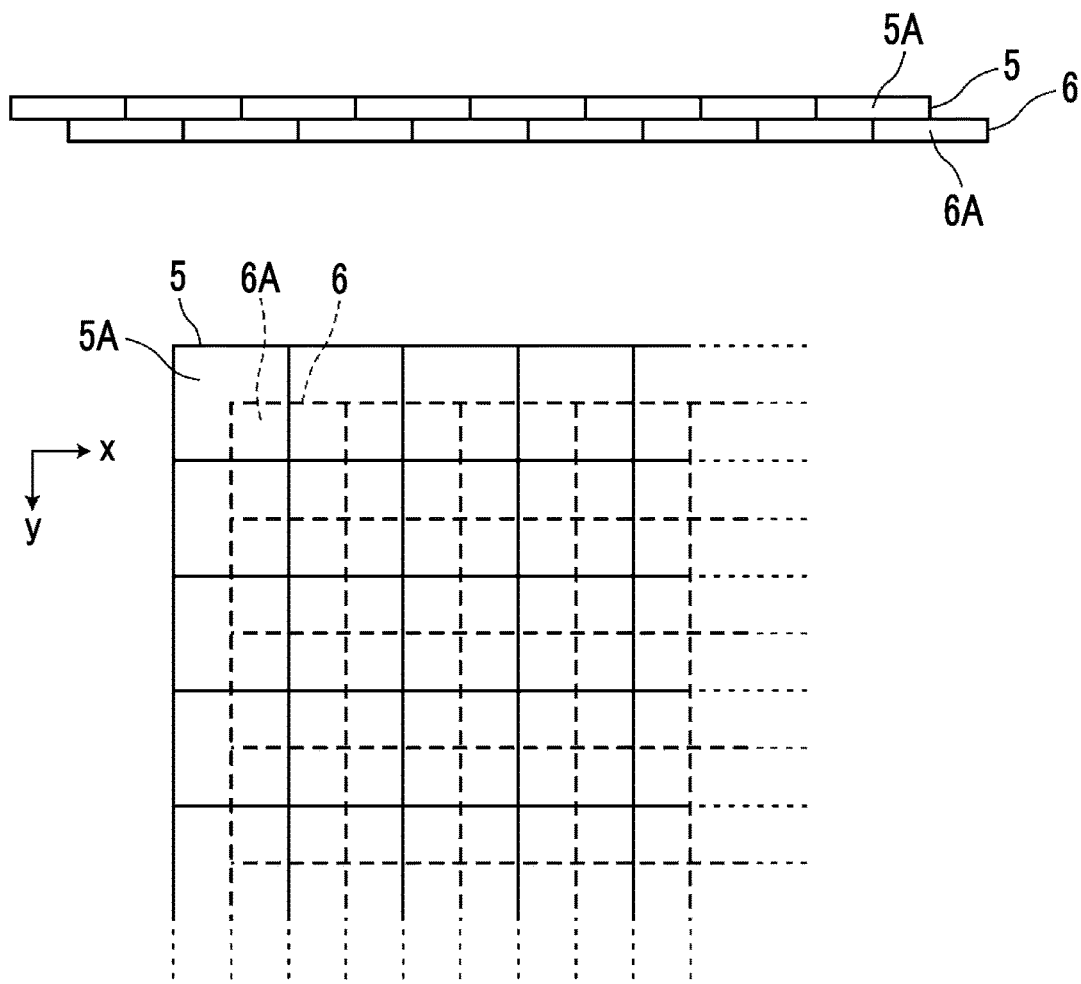
FIG. 3 is a diagram illustrating a state in which first and second radiation detectors overlap each other.

In this embodiment, the second radiation detector 6 overlaps the first radiation detector 5 so as to deviate from the first radiation detector 5 by a half pixel. FIG. 3 is a diagram illustrating an overlap state between the first and second radiation detectors. In FIG. 3, the upper diagram is a side view and the lower diagram is a plan view. In FIG. 3, for convenience of description, the pixel size of each of the radiation detectors 5 and 6 is enlarged. In addition, in the lower diagram of FIG. 3, the first radiation detector 5 is represented by a solid line and the second radiation detector 6 is represented by a dashed line. As illustrated in FIG. 3, each pixel 5A of the first radiation detector 5 and each pixel 6A of the second radiation detector 6 overlap each other so as to deviate by half of the pixel size, that is, a half pixel in two directions, that is, in the x direction and the y direction in FIG. 3.

The image acquisition unit 31 drives the X-ray source 3 to irradiate the object H with X-rays and the first and second radiation detectors 5 and 6 detect the X-rays transmitted through the object H and acquire the first and second radiographic images G1 and G2, respectively. In addition, the first and second radiographic images G1 and G2 may be acquired by a program different from the radiographic image processing program and then stored in the storage 23. In this case, the image acquisition unit 31 reads out the first and second radiographic images G1 and G2 stored in the storage 23 from the storage 23 for image processing.

The corresponding positional relationship acquisition unit 32 acquires the corresponding positional relationship between the position of the pixels of the first radiographic image G1 and the position of the pixels of the second radiographic image G2. Specifically, the corresponding positional relationship acquisition unit 32 acquires, as the corresponding positional relationship, parameters of a magnification power m, an in-plane rotation angle θ, and the amount of shift (Δx, Δy) in the two-dimensional direction in the following Expression (1) for matching feature points in the second radiographic image G2 with feature points in the first radiographic image G1, using common feature points included in the first radiographic image G1 and the second radiographic image G2. In Expression (1), $(x_1, y_1)$ and $(x_2, y_2)$ indicate the pixel position of the feature points in the first and second radiographic images G1 and G2, respectively.

$$\begin{pmatrix} x_1 \\ y_1 \end{pmatrix} = m \begin{pmatrix} \cos\theta & \sin\theta \\ -\sin\theta & \cos\theta \end{pmatrix} \begin{pmatrix} x_2 \\ y_2 \end{pmatrix} + \begin{pmatrix} \Delta_x \\ \Delta_y \end{pmatrix} \quad \text{Expression (1)}$$

In addition, when the image of the object H is captured, an image of a marker may also be captured and the corresponding positional relationship indicated by the above-mentioned Expression (1) may be acquired such that the images of the marker included in the first and second radiographic images G1 and G2 are matched with each other.

Figure 4:
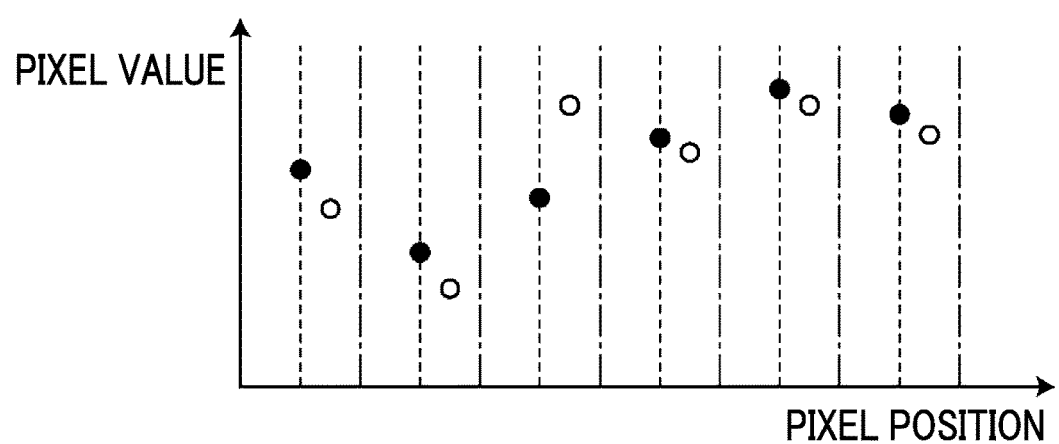
FIG. 4 is a diagram illustrating the relationship between the position of pixels of a first radiographic image and the position of pixels of a second radiographic image.

The resolution enhancement unit 33 estimates a pixel value corresponding to the position between the pixels of the first radiographic image G1 on the basis of the corresponding positional relationship and the pixel values of the first and second radiographic images G1 and G2 and generates the processed radiographic image Gp having a higher resolution than the first and second radiographic images G1 and G2. Here, in this embodiment, the first radiation detector 5 and the second radiation detector 6 overlap each other so as to deviate by a half pixel. Therefore, the pixel of the second radiographic image G2 is located at a position (hereinafter, referred to as a middle position between pixels) where a region between the center positions of the pixels of the first radiographic image G1 is bisected. However, the X-rays emitted from the X-ray source 3 are not parallel beams, but are cone beams. Therefore, particularly, in the periphery of the first and second radiation detectors, in many cases, the pixel of the second radiographic image G2 is not located in the middle between the pixels of the first radiographic image G1 as illustrated in FIG. 4. For simplicity of explanation, the position of the pixels is one-dimensionally illustrated in FIG. 4. In addition, the pixel value of the first radiographic image G1 is represented by a black circle and the pixel value of the second radiographic image G2 is represented by a white circle. A dashed line indicates the center position of the pixel of the first radiographic image G1 and a one-dot chain line indicates the middle position between the pixels of the first radiographic image G1.

Figure 5:
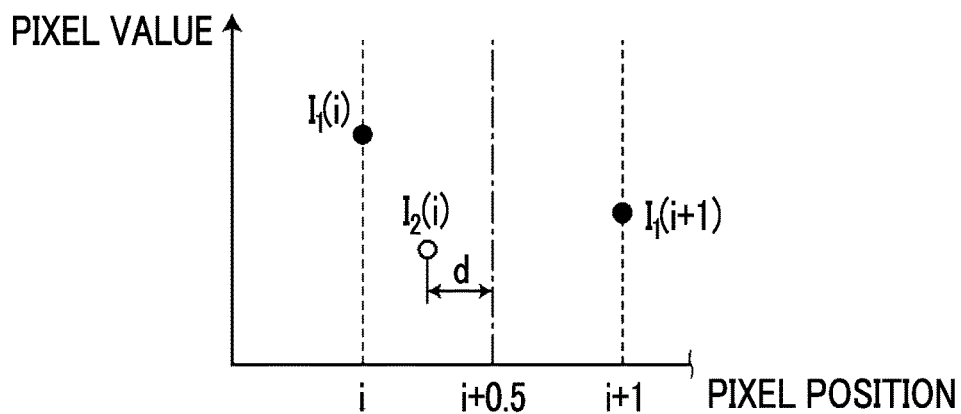
FIG. 5 is a diagram illustrating the calculation of a pixel value.
Figure 6:
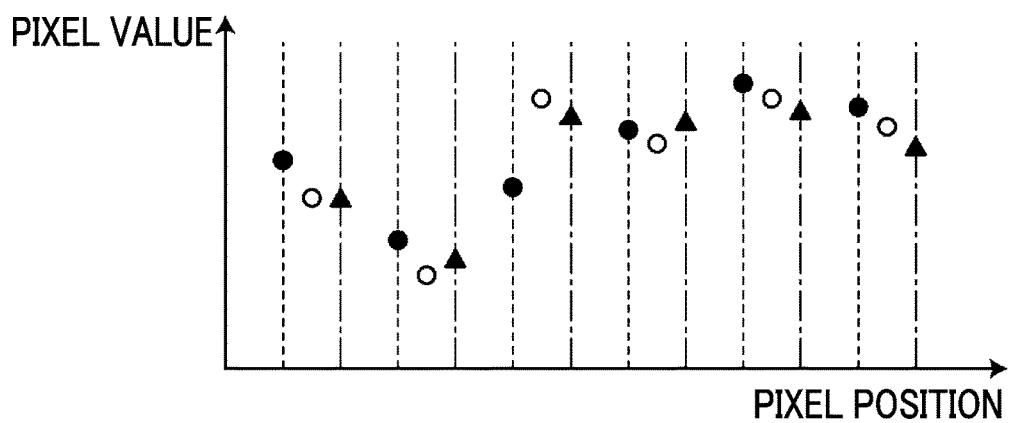
FIG. 6 is a diagram illustrating a pixel value of a processed radiographic image.

In this embodiment, the pixel value of the middle position between the pixels of the first radiographic image G1 is calculated from the second radiographic image G2. FIG. 5 is a diagram illustrating the calculation of the pixel value. In FIG. 5, for simplicity of explanation, the position of the pixel is one-dimensionally illustrated. In FIG. 5, $I_1(i)$ is a pixel value at a pixel position i of the first radiographic image G1, $I_1(i+1)$ is a pixel value at a pixel position i+1 of the first radiographic image G1, i+0.5 is a middle position between the pixel position i and the pixel position i+1, and $I_2(i)$ is a pixel value at a pixel position i of the second radiographic image G2 which corresponds to the pixel position i of the first radiographic image G1. In addition, d is the distance of the pixel position of the second radiographic image G2, which corresponds to the pixel position i of the first radiographic image G1, from the pixel position i+0.5 of the first radiographic image G1. The value of d is calculated on the basis of the corresponding positional relationship acquired by the corresponding positional relationship acquisition unit 32. The resolution enhancement unit 33 calculates a pixel value $I_1(i+0.5)$ using the following Expression (2). Then, as illustrated in FIG. 6, a pixel value corresponding to the middle position between the pixels of the first radiographic image G1 is estimated and the processed radiographic image Gp is generated. In FIG. 6, the estimated pixel value is represented by a black triangle.

$$I_1(i+0.5) = d \times \frac{I_1(i) + I_1(i+1)}{2} + (1-d) \times I_2(i) \quad \text{Expression (2)}$$

In a case in which the pixel position i+0.5 of the first radiographic image G1 is matched with the pixel position i of the second radiographic image G2, d is 0 and the pixel value $I_1(i+0.5)$ is $I_2(i)$. The resolution enhancement unit 33 calculates a pixel value corresponding to the middle position between the pixels of the first radiographic image G1 in this way and generates the processed radiographic image Gp. The number of pixels of the processed radiographic image Gp is four times (=2×2) greater than the number of pixels of the first radiographic image G1.

Figure 7:
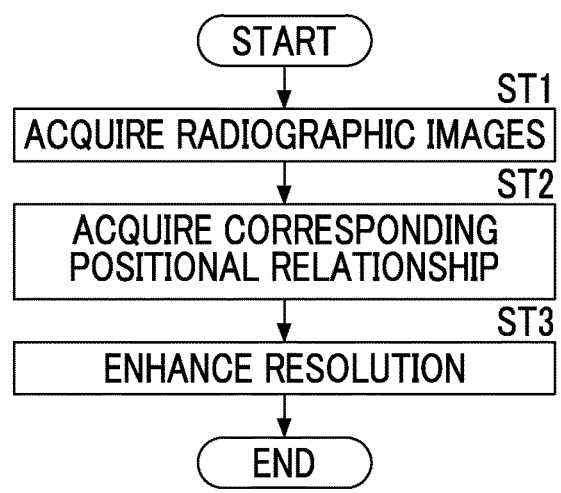
FIG. 7 is a flowchart illustrating a process that is performed in the first embodiment.

Next, a process that is performed in the first embodiment will be described. FIG. 7 is a flowchart illustrating the process performed in the first embodiment. First, the image acquisition unit 31 directs the imaging apparatus 1 to perform imaging and acquires the first radiographic image G1 and the second radiographic image G2 (Step ST1). Then, the corresponding positional relationship acquisition unit 32 acquires the corresponding positional relationship between the position of the pixels of the first radiographic image G1 and the position of the pixels of the second radiographic image G2 (Step ST2). Then, the resolution enhancement unit 33 estimates a pixel value corresponding to the position between the pixels of the first radiographic image G1 on the basis of the corresponding positional relationship and the pixel values of the first and second radiographic images G1 and G2 and generates the processed radiographic image Gp having a higher resolution than the first and second radiographic images G1 and G2 (resolution enhancement: Step ST3). Then, the process ends.

As such, in this embodiment, the first and second radiographic images G1 and G2 acquired by irradiating two radiation detectors 5 and 6 that overlap each other so as to deviate by a half pixel with the X-rays which have been emitted from the X-ray source 3 and then transmitted through the object H are acquired and the corresponding positional relationship between the positions of the pixels of the first and second radiographic images G1 and G2 is acquired. Then, a pixel value corresponding to the position between the pixels of the first radiographic image G1 is estimated on the basis of the corresponding positional relationship, the pixel value of the first radiographic image G1, and the pixel value of the second radiographic image G2 and the processed radiographic image Gp having a higher resolution than the first and second radiographic images G1 and G2 is generated. Here, since two radiation detectors 5 and 6 overlap each other so as to deviate by a half pixel, the probability that each pixel of the second radiographic image G2 will be located between the pixels of the first radiographic image G1 is high. As such, the use of the pixel value of the second radiographic image G2 makes it possible to generate a processed image with high resolution and high sharpness, without increasing the amount of radiation emitted to the object H.

In this embodiment, the pixel size of the radiation detectors 5 and 6 is equal to or greater than 200 μm and equal to or less than 400 μm and is about two times larger than the reference pixel size. Therefore, it is possible to increase the amount of radiation emitted to each pixel. As a result, it is possible to improve the granularity of the first and second radiographic images G1 and G2 and the processed radiographic image Gp and thus to generate the processed radiographic image Gp with a high S/N ratio. In a case in which the pixel size of the radiation detectors 5 and 6 increases, resolution is reduced. However, since the pixel value corresponding to the position between the pixels of the first radiographic image G1 is estimated on the basis of the corresponding positional relationship, the pixel value of the first radiographic image G1, and the pixel value of the second radiographic image G2, it is possible to generate the processed radiographic image Gp with high resolution.

Figure 8:
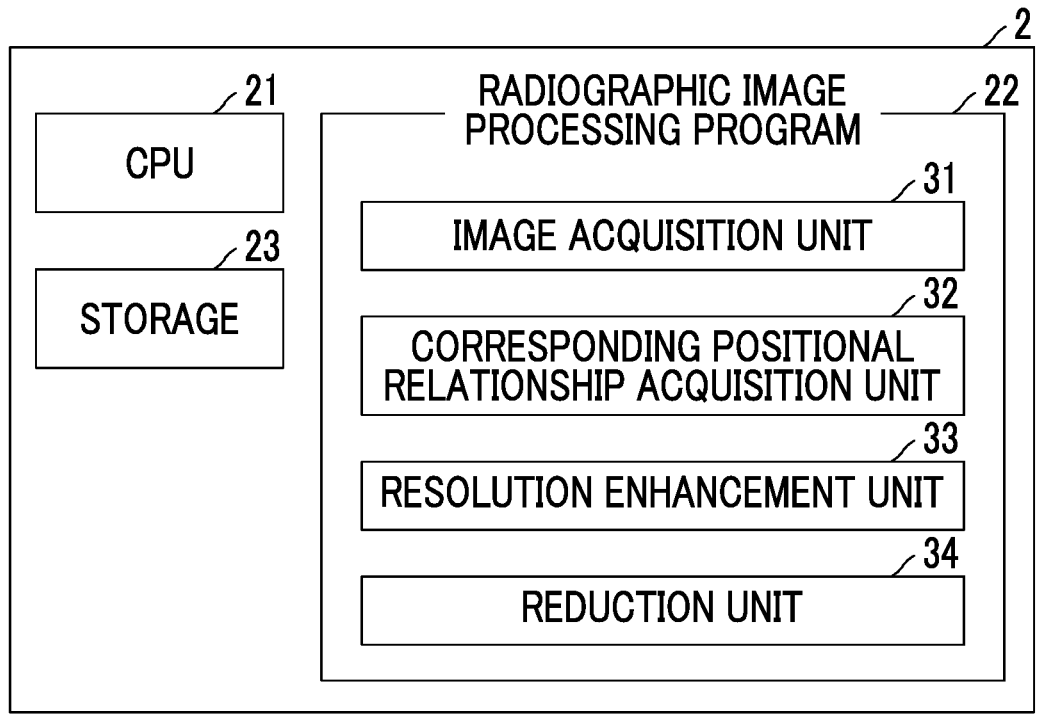
FIG. 8 is a diagram schematically illustrating the configuration of a radiographic image processing apparatus according to a second embodiment.

Next, a second embodiment of the invention will be described. FIG. 8 is a diagram schematically illustrating the configuration of a radiographic image processing apparatus according to a second embodiment of the invention. In the second embodiment, the same components as those in the first embodiment are denoted by the same reference numerals and the detailed description thereof will not be repeated. As illustrated in FIG. 8, the radiographic image processing apparatus according to the second embodiment differs from the radiographic image processing apparatus according to the first embodiment in that it further includes a reduction unit 34 which performs filtering for the processed radiographic image Gp using a smoothing filter and reduces the size of a filtered radiographic image Gp1 so as to be equal to the size of the first radiographic image G1 or the second radiographic image G2 to generate a reduced radiographic image Gp2. In addition, in the second embodiment, it is assumed that the pixel size of the radiation detectors 5 and 6 is the pixel size of a general radiation detector, that is, a reference pixel size.

Figure 9:
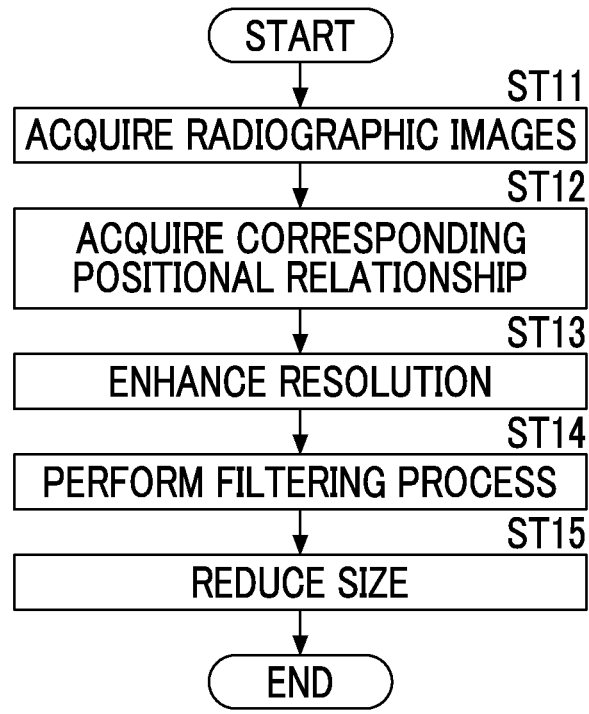
FIG. 9 is a flowchart illustrating a process that is performed in the second embodiment.

Next, a process that is performed in the second embodiment will be described. FIG. 9 is a flowchart illustrating the process performed in the second embodiment. First, the image acquisition unit 31 directs the imaging apparatus 1 to perform imaging and acquires the first radiographic image G1 and the second radiographic image G2 (Step ST11). Then, the corresponding positional relationship acquisition unit 32 acquires the corresponding positional relationship between the position of the pixels of the first radiographic image G1 and the position of the pixels of the second radiographic image G2 (Step ST12). Then, the resolution enhancement unit 33 estimates a pixel value corresponding to the position between the pixels of the first radiographic image G1 on the basis of the corresponding positional relationship and the pixel values of the first and second radiographic images G1 and G2 and generates the processed radiographic image Gp having a higher resolution than the first and second radiographic images G1 and G2 (resolution enhancement: Step ST13). Then, the reduction unit 34 performs a filtering process for the processed radiographic image Gp, using a smoothing filter, such as a Gaussian filter (Step ST14), thins out pixels to reduce the size of the filtered radiographic image Gp1 by half, and generates a reduced radiographic image Gp2 (Step ST15). Then, the process ends.

As such, in the second embodiment, filtering is performed for the processed radiographic image Gp, using the smoothing filter. Therefore, it is possible to improve the granularity of the processed image, without increasing the pixel size of the radiation detectors 5 and 6, and to improve an S/N ratio. In addition, the size of the filtered radiographic image Gp1 is reduced so as to be equal to the size of the first radiographic image G1 or the second radiographic image G2 to generate the reduced radiographic image Gp2 having the same resolution as the first and second radiographic images.

Next, the operation and effect of this embodiment will be described.

The pixel size of the first and second detection unit can be increased to increase the amount of radiation emitted to each pixel. Therefore, it is possible to improve the granularity of the acquired first and second radiographic images and the processed radiographic image and to generate a processed radiographic image with a high S/N ratio. In a case in which the pixel size of the first and second detection unit increases, resolution is reduced. However, since the pixel value corresponding to the position between the pixels of the first radiographic image is estimated on the basis of the corresponding positional relationship, the pixel value of the first radiographic image, and the pixel value of the second radiographic image, it is possible to generate a processed image with high resolution.

Filtering is performed for the processed radiographic image using the smoothing filter. Therefore, it is possible to improve the granularity of the processed image, without increasing the pixel size of the first and second detection unit, and to improve an S/N ratio. In addition, the size of the processed radiographic image is reduced so as to be equal to the size of the first radiographic image or the second radiographic image to generate a reduced radiographic image having the same resolution as the first and second radiographic images.

What is claimed is:

1. A radiographic image processing apparatus comprising:
   a processor that is programmed to:
   acquire a first radiographic image and a second radiographic image respectively acquired from a first detection unit and a second detection unit that overlaps the first detection unit so as to deviate from the first detection unit by a half pixel, by irradiating the first detection unit and the second detection unit with radiation that has been emitted from a radiation source and transmitted through an object;
   acquire a corresponding positional relationship between a position of pixels of the first radiographic image and a position of pixels of the second radiographic image; and
   enhance resolution by:
      calculating a distance between a middle position between the pixels of the first radiographic image and at least one pixel, which corresponds to the middle position between the pixels of the first radiographic image, in the second radiographic image on the basis of the corresponding positional relationship,
      calculating an average pixel value of pixel values of pixels of the first radiographic image which surround the middle position in the first radiographic image as a first pixel value,
      obtaining at least one pixel value of the pixel of the second radiographic image, which corresponds to the middle position between the pixels of the first radiographic image, in the second radiographic image as a second pixel value,
      estimating a pixel value corresponding to the middle position between the pixels of the first radiographic image by weighting the first pixel value and the second pixel value according to the calculated distance, and
      generating a processed radiographic image having a higher resolution than the first and second radiographic images.

2. The radiographic image processing apparatus according to claim 1,
   wherein the processor is programmed to weight the pixel values of the first radiographic image and the second radiographic image according to a distance between the middle position of the first radiographic image and at least one pixel, which corresponds to the position between the pixels of the first radiographic image, in the second radiographic image, and the processor is programmed to estimate the pixel value corresponding to the position between the pixels of the first radiographic image.

3. The radiographic image processing apparatus according to claim 1,
wherein a pixel size of the first and second detection unit is equal to or greater than 200 μm and equal to or less than 400 μm.

4. The radiographic image processing apparatus according to claim 1, wherein the processor is programmed to:
perform filtering for the processed radiographic image, using a smoothing filter, and reduce a size of the processed radiographic image so as to be equal to a size of the first radiographic image or the second radiographic image to generate a reduced radiographic image.

5. A radiographic image processing method comprising:
acquiring a first radiographic image and a second radiographic image respectively acquired from a first detection unit and a second detection unit which that overlaps the first detection unit so as to deviate from the first detection unit by a half pixel, by irradiating the first detection unit and the second detection unit with radiation that has been emitted from a radiation source and transmitted through an object;
acquiring a corresponding positional relationship between a position of pixels of the first radiographic image and a position of pixels of the second radiographic image; and
calculating a distance between a middle position between the pixels of the first radiographic image and at least one pixel, which corresponds to the middle position between the pixels of the first radiographic image, in the second radiographic image on the basis of the corresponding positional relationship, calculating an average pixel value of pixel values of pixels of the first radiographic image which surround the middle position in the first radiographic image as a first pixel value, obtaining at least one pixel value of the pixel of the second radiographic image, which corresponds to the middle position between the pixels of the first radiographic image, in the second radiographic image as a second pixel value, estimating a pixel value corresponding to the middle position between the pixels of the first radiographic image by weighting the first pixel value and the second pixel value according to the calculated distance, and generating a processed radiographic image having a higher resolution than the first and second radiographic images.

6. A non-transitory computer-readable storage medium that stores a radiographic image processing program that causes a computer to perform:
acquiring a first radiographic image and a second radiographic image respectively acquired from a first detection unit and a second detection unit that overlaps the first detection unit so as to deviate from the first detection unit by a half pixel, by irradiating the first detection unit and the second detection unit with radiation that has been emitted from a radiation source and transmitted through an object;
acquiring a corresponding positional relationship between a position of pixels of the first radiographic image and a position of pixels of the second radiographic image; and
calculating a distance between a middle position between the pixels of the first radiographic image and at least one pixel, which corresponds to the middle position between the pixels of the first radiographic image, in the second radiographic image on the basis of the corresponding positional relationship, calculating an average pixel value of pixel values of pixels of the first radiographic image which surround the middle position in the first radiographic image as a first pixel value, obtaining at least one pixel value of the pixel of the second radiographic image, which corresponds to the middle position between the pixels of the first radiographic image, in the second radiographic image as a second pixel value, estimating a pixel value corresponding to the middle position between the pixels of the first radiographic image by weighting the first pixel value and the second pixel value according to the calculated distance, and generating a processed radiographic image having a higher resolution than the first and second radiographic images.

* * * * *